United States Patent
Fuseya et al.

(10) Patent No.: US 11,331,459 B2
(45) Date of Patent: May 17, 2022

(54) DILATOR

(71) Applicant: ASAHI INTECC CO., LTD., Seto (JP)

(72) Inventors: Yukihiro Fuseya, Seto (JP); Hideaki Maki, Seto (JP); Daiki Takahashi, Seto (JP); Akira Sawai, Seto (JP); Marina Kitai, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 68 days.

(21) Appl. No.: 16/580,301

(22) Filed: Sep. 24, 2019

(65) Prior Publication Data

US 2020/0016386 A1    Jan. 16, 2020

Related U.S. Application Data

(63) Continuation of application No. PCT/JP2018/011673, filed on Mar. 23, 2018.

(30) Foreign Application Priority Data

Mar. 24, 2017   (WO) .................. PCT/JP2017/012024

(51) Int. Cl.
*A61M 29/00* (2006.01)
*A61M 25/06* (2006.01)
(Continued)

(52) U.S. Cl.
CPC .......... *A61M 29/00* (2013.01); *A61M 25/008* (2013.01); *A61M 25/0023* (2013.01);
(Continued)

(58) Field of Classification Search
CPC .......... A61M 16/0472; A61M 16/0429; A61M 2025/0687; A61M 2025/006;
(Continued)

(56) References Cited

U.S. PATENT DOCUMENTS

| | | | | |
|---|---|---|---|---|
| 207,932 A | * | 9/1878 | Alvord | A61B 17/12022 606/191 |
| 4,848,342 A | * | 7/1989 | Kaltenbach | A61M 29/02 606/198 |

(Continued)

FOREIGN PATENT DOCUMENTS

| | | |
|---|---|---|
| JP | S60-234671 A | 11/1985 |
| JP | 2502565 Y2 | 6/1996 |

(Continued)

OTHER PUBLICATIONS

May 29, 2018 International Search Report issued in International Patent Application No. PCT/JP2018/011673.

*Primary Examiner* — Jocelin C Tanner
(74) *Attorney, Agent, or Firm* — Oliff PLC

(57) ABSTRACT

A dilator includes a shaft with a tapered portion having an outer diameter that is smaller at a distal end than at a proximal end; a proximal end portion provided at a proximal end side of the tapered portion; and optionally a distal end portion provided at a distal end side of the tapered portion. Pitches of adjacent portions of the spirally-arranged protruding portion provided on the tapered portion are different (either smaller or larger) than those of adjacent portions of the spirally-arranged protruding portion provided on distal end side of the proximal end portion and/or on the distal end portion.

7 Claims, 4 Drawing Sheets

(51) Int. Cl.
*A61M 25/00* (2006.01)
*A61B 17/34* (2006.01)

(52) U.S. Cl.
CPC .... *A61M 25/0052* (2013.01); *A61M 25/0053* (2013.01); *A61M 25/0662* (2013.01); *A61B 2017/3458* (2013.01); *A61M 25/005* (2013.01); *A61M 2025/006* (2013.01); *A61M 2025/0687* (2013.01)

(58) Field of Classification Search
CPC .............. A61M 29/00; A61M 25/0662; A61M 25/008; A61M 25/0053; A61M 25/0052; A61M 25/005; A61M 25/0023; A61M 2029/025; A61B 2090/3966; A61B 2017/3458; A61B 2017/3456; A61B 2017/00915; A61B 90/02; A61B 17/3417
See application file for complete search history.

(56) References Cited

U.S. PATENT DOCUMENTS

| | | | | |
|---|---|---|---|---|
| 5,098,374 | A * | 3/1992 | Othel-Jacobsen | A61F 2/94 604/8 |
| 5,211,636 | A * | 5/1993 | Mische | A61M 25/09 600/585 |
| 5,303,714 | A | 4/1994 | Abele et al. | |
| 5,630,813 | A | 5/1997 | Kieturakis | |
| 8,273,100 | B2 * | 9/2012 | Martinez | A61B 17/12113 606/200 |
| 2001/0052721 | A1 | 12/2001 | Tanaka | |
| 2002/0077655 | A1 * | 6/2002 | Frova | A61M 16/0429 606/196 |
| 2003/0069522 | A1 | 4/2003 | Jacobsen et al. | |
| 2005/0165405 | A1 | 7/2005 | Tsou | |
| 2006/0235455 | A1 | 10/2006 | Oshida | |
| 2007/0088230 | A1 | 4/2007 | Terashi et al. | |
| 2008/0097247 | A1 | 4/2008 | Eskuri | |
| 2009/0005814 | A1 | 1/2009 | Miller et al. | |
| 2009/0281500 | A1 * | 11/2009 | Acosta | A61M 25/0102 604/167.01 |
| 2010/0076264 | A1 | 3/2010 | Tallarida et al. | |
| 2011/0098531 | A1 | 4/2011 | To | |
| 2011/0144681 | A1 | 6/2011 | Whitman et al. | |
| 2011/0213316 | A1 | 9/2011 | Ibrahim et al. | |
| 2012/0004606 | A1 * | 1/2012 | Lentz | A61M 25/0053 604/103.04 |
| 2012/0029281 | A1 | 2/2012 | Frassica et al. | |
| 2012/0116350 | A1 | 5/2012 | Strauss et al. | |
| 2013/0090523 | A1 * | 4/2013 | Van Bladel | A61B 17/12013 600/37 |
| 2013/0274782 | A1 * | 10/2013 | Morgan | A61B 17/3494 606/185 |
| 2014/0046357 | A1 * | 2/2014 | Neoh | A61M 29/00 606/191 |
| 2015/0094543 | A1 | 4/2015 | Whittaker et al. | |
| 2016/0024343 | A1 | 1/2016 | Nakai et al. | |
| 2016/0287849 | A1 | 10/2016 | Hodson | |
| 2017/0296221 | A1 | 10/2017 | Di Caprio et al. | |
| 2020/0016385 | A1 * | 1/2020 | Fuseya | A61M 25/0053 |
| 2020/0016386 | A1 | 1/2020 | Fuseya et al. | |
| 2020/0016387 | A1 | 1/2020 | Fuseya et al. | |
| 2021/0001097 | A1 * | 1/2021 | Fuseya | A61M 25/008 |

FOREIGN PATENT DOCUMENTS

| | | |
|---|---|---|
| JP | 2000-057852 A | 2/2000 |
| JP | 2001-286963 A | 10/2001 |
| JP | 2002-177289 A | 6/2002 |
| JP | 2004-009844 A | 1/2004 |
| JP | 2005-118102 A | 5/2005 |
| JP | 2006-130073 A | 5/2006 |
| JP | 2007-501102 A | 1/2007 |
| JP | 2007-098120 A | 4/2007 |
| JP | 2008-011867 A | 1/2008 |
| JP | 2010-540072 A | 12/2010 |
| JP | 2012-095812 A | 5/2012 |
| JP | 2012-100827 A | 5/2012 |
| JP | 2012-179222 A | 9/2012 |
| JP | 2012-183125 A | 9/2012 |
| JP | 2014-136047 A | 7/2014 |
| JP | 2014-524807 A | 9/2014 |
| JP | 5991951 B2 | 9/2016 |
| JP | 2017-051328 A | 3/2017 |
| JP | 2017-523019 A | 8/2017 |
| JP | 2018-033985 A | 3/2018 |
| WO | 91/07202 A1 | 5/1991 |
| WO | 2004/066827 A3 | 8/2004 |
| WO | 2009/045276 A1 | 4/2009 |
| WO | 2010/123825 A1 | 10/2010 |
| WO | 2013/038720 A1 | 3/2013 |
| WO | 2015/032727 A1 | 3/2015 |
| WO | 2016/018434 A1 | 2/2016 |
| WO | 2018/180209 A1 | 10/2018 |

* cited by examiner

DILATOR

CROSS REFERENCE TO RELATED APPLICATION

This application is a continuation application of International Application No. PCT/JP2018/011673, filed Mar. 23, 2018, which claims priority to International Application No. PCT/JP2017/012024, filed Mar. 24, 2017. The contents of these applications are incorporated herein by reference in their entirety.

BACKGROUND

The present disclosure relates to a dilator.

Dilators are known for expanding a hole formed on the wall of the patient's digestive tract and the like for the purpose of treatment. The distal end of a dilator is inserted into a hole formed on a wall, and a tapered portion is then pushed into the hole to expand the hole. Such a dilator is disclosed in, for example, Japanese Patent Application Laid-Open No. 2008-11867.

SUMMARY

When the dilator as described above is very long, a rotational force and a pushing force from the hand (proximal) side may not be well transmitted to the distal end of the dilator, and thus a hole formed on the wall of the digestive tract cannot be sufficiently expanded.

An object of the disclosed embodiments is to provide a dilator capable of easily increasing the diameter of a hole formed on the wall of the digestive tract and the like.

In order to achieve the above object, a dilator according to the disclosed embodiments includes a hollow shaft and a grip portion provided at a proximal end of the shaft. The shaft includes a tapered portion having an outer diameter that is smaller at a distal end than at a proximal end; and a proximal end portion provided at a proximal end side of the tapered portion and extending to the proximal end side. The shaft may optionally further include a distal end portion provided at a distal end side of the tapered portion and extending to the distal end side. A spirally-arranged protruding portion is provided on an outer peripheral surface of the shaft, and has gaps between adjacent portions of the spirally-arranged protruding portion along a longitudinal axis of the shaft.

Pitches of adjacent portions of the spirally-arranged protruding portion provided on the tapered portion may be different than pitches of adjacent portions of the spirally-arranged protruding portion provided on the proximal end portion and/or distal end portion.

For example, the spirally-arranged protruding portion provided on the tapered portion may be smaller than the pitches of adjacent portions of the spirally-arranged protruding portion provided on the proximal end portion (and/or the distal end portion, when included). Thus, when the shaft does not include the distal end portion, the pitches of adjacent portions of the spirally-arranged protruding portion provided on the tapered portion are smaller than those of adjacent portions of the spirally-arranged protruding portion provided on the proximal end portion. When the shaft has the distal end portion, the pitches of adjacent portions of the spirally-arranged protruding portion provided on the tapered portion are smaller than those of adjacent portions of the spirally-arranged protruding portion provided on the distal end portion, the proximal end portion, or both.

Or the spirally-arranged protruding portion provided on the tapered portion may be larger than the pitches of adjacent portions of the spirally-arranged protruding portion provided on the proximal end portion (and/or the distal end portion, when included). Thus, when the shaft does not have the distal end portion, the pitches of adjacent portions of the spirally-arranged protruding portion provided on the tapered portion are larger than those of adjacent portions of the spirally-arranged protruding portion provided on the proximal end portion. When the shaft has the distal end portion, the pitches of adjacent portions of the spirally-arranged protruding portion provided on the tapered portion are larger than those of adjacent portions of the spirally-arranged protruding portion provided on the distal end portion, the proximal end portion, or both.

Further, the shaft may include a first coil having a wire wound around into a hollow shape.

Further, the spirally-arranged protruding portion may include a second coil having a wire wound around on the outer peripheral surface of the shaft.

When the shaft includes the first coil and the spirally-arranged protruding portion includes the second coil, the wire of the first coil may be wound around in a direction opposite to the wire of the second coil.

DETAILED DESCRIPTION OF EMBODIMENTS

Below, embodiments of the present invention will be described with reference to the figures. It is noted that the dimensions of dilators shown in the figures are provided to merely facilitate understanding of the embodiments, but do not necessarily correspond to the actual dimensions.

Figure 1:
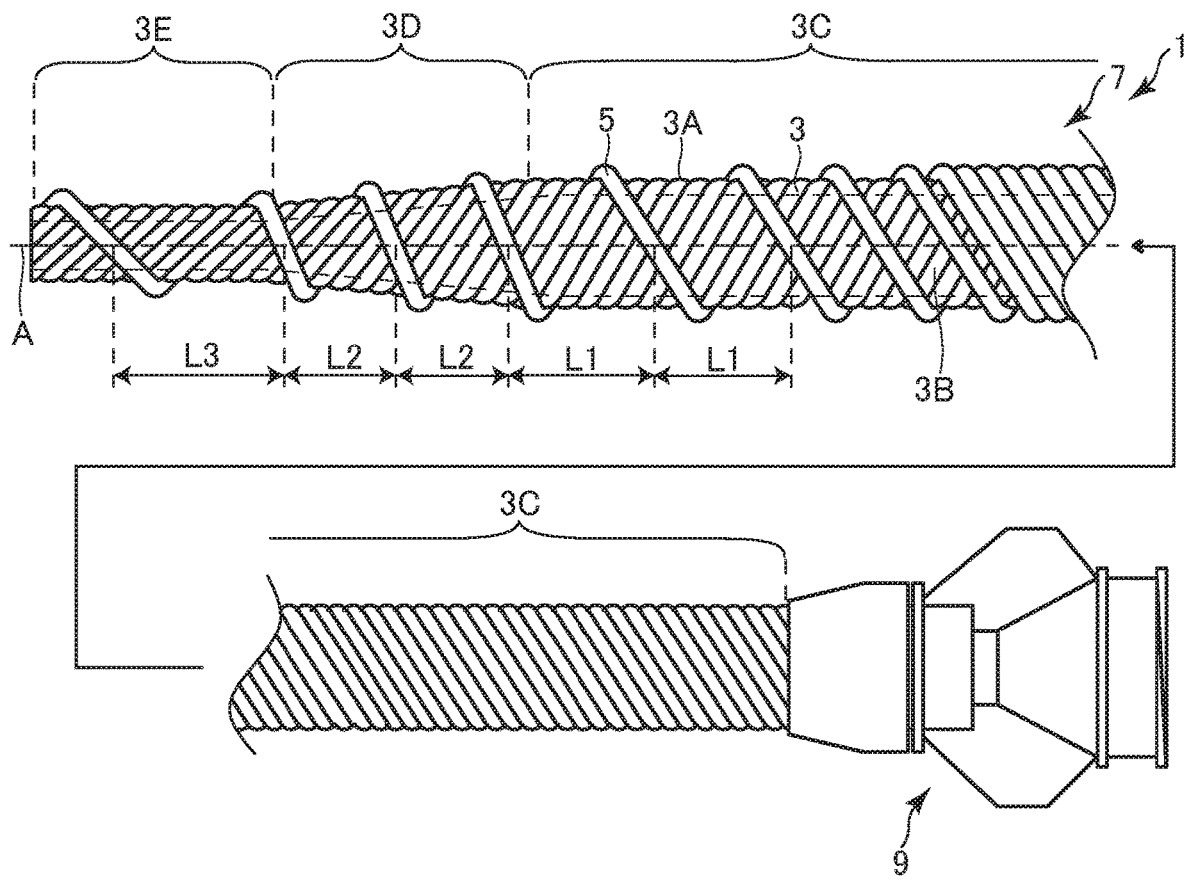
FIG. 1 shows an overall view of a dilator according to the disclosed embodiments.

FIG. 1 shows an overall view of a dilator 1 according to the disclosed embodiments.

In FIG. 1, the left side in the figure corresponds to the front end side (the distal side) which is to be inserted into the body, and the right side corresponds to the base end side (the hand side, the proximal side) which is to be operated by an operator such as a surgeon.

In FIG. 1, the dilator 1 includes a multilayer body 7 including a first coil 3 having a plurality of wires wound around into a hollow shape and a second coil 5 having a single wire wound around on an outer peripheral surface 3A of the first coil 3 in a direction (clockwise, facing to the distal end) opposite to the first coil 3 (counterclockwise, facing to the distal end); and a connector 9 having a hollow shape and connected to a proximal end of the multilayer body 7.

The wires of the first coil 3 and the second coil 5 are, for example, metal wires of stainless steel, a superelastic alloy such as nickel-titanium, and the like, or resin wires. Herein, the wires will be referred to as metal wires for the sake of example.

The first coil 3 is configured such that 10 metal wires (e.g., stainless steel wires) are wound around. The first coil 3 has a hollow shape in which an inner cavity 3B is formed penetratingly extending from a proximal end to a distal end. The first coil 3 has a proximal end portion 3C, a tapered portion 3D, and a distal end portion 3E. The first coil 3 corresponds to a shaft.

The proximal end portion 3C is located in the proximal end side of the dilator 1, and the connector 9 is connected to a proximal end thereof. Further, the proximal end portion 3C has a substantially constant outer diameter from the proximal end thereof through a distal end.

The tapered portion 3D is located at the distal end side of the proximal end portion 3C, and extends to the distal end side from the distal end of the proximal end portion 3C, and is configured so as to have an outer diameter that is smaller toward the distal end side.

The distal end portion 3E is located at the distal end side of the tapered portion 3D, and extends to the distal end side from a distal end of the tapered portion 3D. The distal end portion 3E has a substantially constant outer diameter from a proximal end thereof through a distal end. As described above, the first coil 3 which corresponds to a shaft has a hollow shape having an outer diameter that is smaller at a distal end than at a proximal end.

The second coil 5 has, for example, a single metal wire wound around on the outer peripheral surface 3A of the first coil 3 in a direction (clockwise, facing to the distal end) opposite to the first coil 3 (counterclockwise, facing to the distal end). Here, the metal wire is wound around closely (with small winding pitch, for example where adjacent portions are in contact with each other) at the proximal end side of the proximal end portion 3C, and wound around with gaps between adjacent windings at the distal end side of the proximal end portion 3C, at the tapered portion 3D, and at the distal end portion 3E. A portion of the second coil 5 wound around with gaps provides a spirally-arranged protruding portion protruding outwardly (protruding radially outward from the outermost portion of the dilator 1, the outermost surface) on the outer peripheral surface 3A of the first coil 3. The above spirally-arranged protruding portion has gaps between adjacent portions (adjacent windings of a metal wire) along an axis A of the first coil 3 (a longitudinal axis of the shaft). The screw action of the above spirally-arranged protruding portion enables the dilator 1 to be moved forward even by a rotational operation of the dilator 1.

Further, pitches (along the axis A) of adjacent portions provided on the tapered portion 3D are configured to be smaller than those of adjacent portions of the second coil 5 provided on the distal end portion 3E and on the distal end side of the proximal end portion 3C. That is, the configuration is such that L1, L3>L2 for the adjacent portions of the second coil 5 wherein L1 represents a pitch at the distal end side of the proximal end portion 3C, L2 represents a pitch at the tapered portion 3D, and L3 represents a pitch at the distal end portion 3E. It is noted that the pitches at the distal end side of the proximal end portion 3C may be same or different. The pitches at the tapered portion 3D may be same or different.

Further, with regard to the metal wire of the second coil 5, the amount of gap (space) between adjacent portions of the metal wire (the length of the gap in a direction of the axis A) is gradually decreased toward the proximal end side thereof at the proximal end portion 3C. This configuration enables the stiffness of the dilator 1 (the multilayer body 7) along the axis direction to be gradually changed so that the dilator 1 can easily enter into an approach pathway even when the pathway meanders.

The length of the dilator is, for example, 2000 mm, preferably 1600 mm to 2500 mm; the length of the distal end portion 3E is, for example, 10 mm, preferably 0 to 100 mm; and the length of the tapered portion 3D is, for example, 30 mm, preferably 5 to 100 mm. The inner diameter of the distal end of the first coil 3 is, for example, 0.7 mm, preferably 0.4 to 1.0 mm; and the inner diameter of the proximal end of the first coil 3 is, for example, 1.5 mm, preferably 1.0 to 3.0 mm. The outer diameter of the distal end of the second coil 5 is, for example, 1.84 mm, preferably 0.8 to 3.0 mm; and the outer diameter of the proximal end of the second coil 5 is, for example, 2.64 mm, preferably 1.4 mm to 5.0 mm. Further, the diameters of the metal wires of the first coil 3 are, for example, 0.21 mm, preferably 0.1 to 0.5 mm; and the diameter of the metal wire of the second coil 5 is, for example, 0.36 mm, preferably 0.1 to 0.5 mm.

Further, the pitches L1 and L3 of the second coil 5 at the proximal end portion 3C and the distal end portion 3E are, for example, 2 mm; and the pitch L2 of the second coil 5 at the tapered portion 3D is, for example, 1.5 mm. The ratio (L2/(L1 or L3)) of them is 0.75. It is noted that the pitches L1 and L3 of the second coil 5 at the proximal end portion 3C and the distal end portion 3E are preferably 0.25 to 5 mm, the pitch L2 of the second coil 5 at the tapered portion 3D is preferably 0.2 to 4 mm, and the ratio (L2/(L1 or L3)) ranges between 0.04 and 1.

The connector 9 as a grip portion is a portion through which an operator pushes the dilator into the body, and/or performs a rotational operation. The connector 9 has a distal end connected to the proximal end of the first coil 3 and the proximal end of the second coil 5. The connector 9 is made of a resin, and has a hollow shape having an inner cavity in communication with the inner cavity 3B of the first coil 3.

In the dilator 1, the spirally-arranged protruding portion (the second coil 5) protruding outwardly is provided on the outer peripheral surface 3A of the first coil 3 which corresponds to a shaft, and has gaps between adjacent portions along the axis direction of the first coil 3. This configuration enables the dilator 1 to be moved forward not only by a conventional pushing operation, but also by a rotational operation of the spirally-arranged protruding portion.

Further, the pitches of adjacent portions of the second coil 5 provided on the tapered portion 3D are configured to be smaller than those of adjacent portions of the second coil 5 provided on the distal end side of the proximal end portion 3C and at the distal end portion 3E. By virtue of this configuration, the frictional resistance with a target matter (for example, the digestive tract such as stomach, and liver) is larger at the tapered portion 3D of the first coil 3 than at the distal end side of the proximal end portion 3C and at the distal end portion 3E when the dilator 1 is rotated. This enables a driving force to be larger at the tapered portion 3D than at the proximal end portion 3C and the distal end portion 3E of the dilator 1, leading to easy expansion of a hole.

Further, a shaft comprised of the first coil 3 including a plurality of metal wires wound around into a hollow shape can improve the flexibility of the shaft and the transmissibility of torque via the first coil 3. Further, a spirally-arranged protruding portion comprised of the second coil 5 having a single metal wire wound around on the outer peripheral surface 3A of the first coil 3 can be easily formed, and can ensure the flexibility of the distal end of the dilator 1 by virtue of the elasticity of the second coil 5, and can improve the torquability. Further, the wires of the first coil 3 are wound around in a direction opposite to the wire of the second coil 5. Therefore, even when the dilator 1 is rotated in a direction to open the first coil 3, a force is applied in a direction to close the second coil 5 to prevent opening of the first coil 3. This allows a force applied to the connector 9 of the dilator 1 to be transmitted to the distal end side.

Next, an example of operating modes of the above dilator will be described.

First, a target matter is punctured with an introducer needle to open a hole. Subsequently, a guide wire is inserted into an inner cavity of the introducer needle, and then the introducer needle is withdrawn.

Next, the proximal end of the guide wire is inserted into an inner cavity of the above dilator, and then the dilator is inserted into the hole. Subsequently, the dilator is pushed in while rotating the shaft to expand the hole. During this, the tapered portion moves forward by virtue of the screw action of the spirally-arranged protruding portion by a rotational operation of the shaft and others, enabling the tapered portion to smoothly expand the hole.

Figure 2:
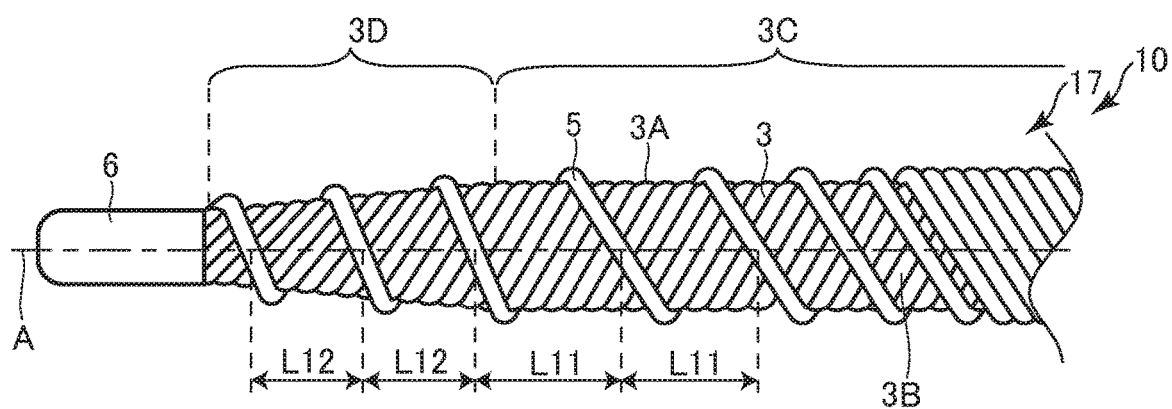
FIG. 2 shows a distal-end side portion of a dilator according to the disclosed embodiments.

FIG. 2 shows a distal-end side portion of a dilator 10 according to the disclosed embodiments.

In FIG. 2, the left side in the figure corresponds to the front end side (the distal side) which is to be inserted into the body, and the right side corresponds to the base end side (the hand side, the proximal side) which is to be operated by an operator such as a surgeon.

It is noted that the dilator 10 basically has the same structure as the dilator 1. Therefore, the same number is given to the same member, and detailed description will be omitted.

In FIG. 2, the dilator 10 includes a multilayer body 17 including the first coil 3 including a plurality of metal wires wound around into a hollow shape and the second coils 5 having a single metal wire wound around on the outer peripheral surface 3A of the first coil 3 in a direction (clockwise, facing to the distal end) opposite to the first coil 3 (counterclockwise, facing to the distal end); and the connector 9 having a hollow shape and connected to a proximal end of the multilayer body 17. However, the dilator 10 differs from the dilator 1 in that the dilator 10 has a distal tip 6 instead of the distal end portion 3E of the first coil 3 of the dilator 1. The first coil 3 having the distal tip 6 provided at the distal end corresponds to a shaft.

The distal tip 6 is formed by casting a solder material (a silver-tin solder material, a gold-tin solder material, or the like) into the distal end of the first coil 3, and has a substantially tubular hollow shape. Further, the distal tip 6 has a flat (smooth) surface while the distal end of the multilayer body 7 has an uneven surface.

Again, the pitches (along the axis A) of adjacent portions of the second coil 5 provided on the tapered portion 3D are configured to be smaller than those of adjacent portions of the second coil 5 provided on the distal end side of the proximal end portion 3C. That is, the configuration is such that L11>L12 for the adjacent portions of the second coil 5 wherein L11 represents a pitch at the distal end side of the proximal end portion 3C, and L12 represents a pitch at the tapered portion 3D.

The dilator 10 having this configuration can produce similar effects as the dilator 1. That is, the frictional resistance with a target matter (for example, the digestive tract such as stomach, and liver) is larger at the tapered portion 3D of the first coil 3 than at the distal end side of the proximal end portion 3C when the dilator 10 is rotated. This enables a driving force to be larger at the tapered portion 3D than at the proximal end portion 3C of the dilator 10, leading to easy expansion of a hole. Further, the distal tip 6 having a flat surface is connected to the distal end of the multilayer body 17. This configuration can further improve insertability into a punctured portion by first pressing the dilator 10 against the punctured portion, and then pushing and rotating the dilator 10 thereinto.

Figure 3:
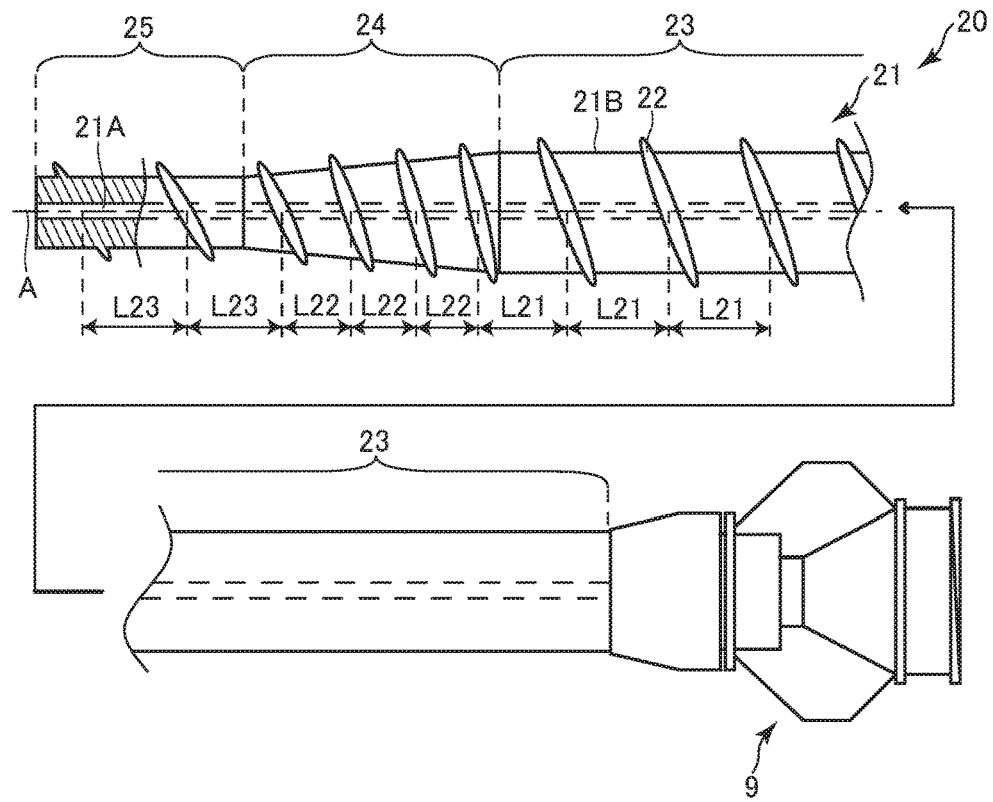
FIG. 3 shows an overall view of a dilator according to the disclosed embodiments.

FIG. 3 shows an overall view of a dilator 20 according to the disclosed embodiments.

In FIG. 3, the left side in the figure corresponds to the front end side (the distal side) which is to be inserted into the body, and the right side corresponds to the base end side (the hand side, the proximal side) which is to be operated by an operator such as a surgeon.

In FIG. 3, the dilator 20 includes a shaft 21, a spirally-arranged protruding portion 22, and the connector 9 connected to a proximal end of the shaft 21.

The shaft 21 has a hollow shape in which an inner cavity 21A is formed penetratingly extending from a proximal end to a distal end. Further, the shaft 21 has a proximal end portion 23, a tapered portion 24, and a distal end portion 25.

There is no particular limitation for materials of the shaft 21 and the spirally-arranged protruding portion 22, as long as they can ensure the flexibility of the tapered portion 24 and the distal end portion 25, and also have biocompatibility. For example, the following materials can be used: stainless steel, superelastic alloy materials such as nickel-titanium alloys, or synthetic resins such as polyvinyl chloride resin, urethane resin, polyolefin resin, polyamide resin, and fluororesin.

The proximal end portion 23 is located in the proximal end side of the dilator 20, and the connector 9 is connected to a proximal end thereof. Further, the proximal end portion 23 is provided proximal to the tapered portion 24, and extends to the proximal end side. The proximal end portion 23 has a substantially constant outer diameter from the proximal end thereof through a distal end.

The tapered portion 24 is connected to the distal end of the proximal end portion 23, and extends from that distal end to the distal end side, and has a shape tapered toward the distal end side.

The distal end portion 25 is connected to a distal end of the tapered portion 24, and extends from that distal end to the distal end side. The distal end portion 25 has a substantially constant outer diameter from a proximal end thereof through a distal end. As described above, the shaft 21 has a hollow shape having an outer diameter that is smaller at a distal end than at a proximal end.

The spirally-arranged protruding portion 22 is provided on an outer peripheral surface 21B of the shaft 21 so as to be protruded outwardly (outermost portion of the dilator 20, the outermost surface). The spirally-arranged protruding portion 22 is provided at a distal-end side portion of the proximal end portion 23, at the tapered portion 24, and at the distal end portion 25, and has gaps between adjacent portions along the axis direction of the shaft 21. That is, the adjacent portions of the spirally-arranged protruding portion 22 are spaced from each other. The spirally-arranged protruding portion 22 is integrally formed with the shaft 21 by casting or the like.

Pitches (along the axis A) of adjacent portions of the spirally-arranged protruding portion 22 provided on the tapered portion 24 are configured to be smaller than those of adjacent portions of the spirally-arranged protruding portion 22 provided at the distal end side of the proximal end portion 23 and at the distal end portion 25. That is, the configuration is such that L21, L23>L22 for the adjacent portions of the spirally-arranged protruding portion 22 wherein L21 represents a pitch at the distal end side of the proximal end portion 23, L22 represents a pitch at the tapered portion 24, and L23 represents a pitch at the distal end portion 25. It is noted that the pitches at the distal end side of the proximal end portion 23 and at the distal end portion 25 may be same or different. The pitches at the tapered portion 24 may be same or different.

In the dilator 20, the spirally-arranged protruding portion 22 protruding outwardly is provided on the outer peripheral surface 21B of the shaft 21, and has gaps between adjacent portions along the axis A of the shaft 21. This configuration enables the dilator 20 to be moved forward not only by a conventional pushing operation, but also by a rotational operation of the spirally-arranged protruding portion 22.

Further, the pitches of adjacent portions of the spirally-arranged protruding portion 22 provided at the tapered portion 24 are configured to be smaller than those of adjacent portions along the axis A of the spirally-arranged protruding portion 22 provided at the distal end side of the proximal end portion 23 and at the distal end portion 25. By virtue of this configuration, the frictional resistance with a target matter (for example, the digestive tract such as stomach, and liver) is larger at the tapered portion 24 of the shaft 21 than at the distal end side of the proximal end portion 24 and at the distal end portion 25 when the dilator 20 is rotated. This enables a driving force to be larger at the tapered portion 24 than at the proximal end portion 24 and the distal end portion 25 of the dilator 20, leading to easy expansion of a hole.

Figure 4:
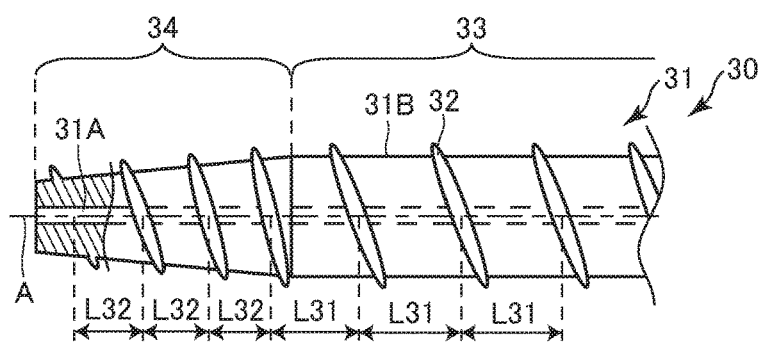
FIG. 4 shows a partial cross-sectional view of a distal-end side portion of a dilator according to the disclosed embodiments.

FIG. 4 shows a partial cross-sectional view of a distal-end side portion of a dilator 30 according to the disclosed embodiments.

In FIG. 4, the left side in the figure corresponds to the front end side (the distal side) which is to be inserted into the body, and the right side corresponds to the base end side (the hand side, the proximal side) which is to be operated by an operator such as a surgeon.

In FIG. 4, the dilator 30 includes a shaft 31, a spirally-arranged protruding portion 32, and the connector 9 connected to a proximal end of the shaft 31 (see FIG. 3). The material(s) of the shaft 31 and the spirally-arranged protruding portion 32 is/are the same as that/those of the shaft 21 and the spirally-arranged protruding portion 22 of the dilator 20.

The shaft 31 has a hollow shape in which an inner cavity 31A is formed penetratingly extending from a proximal end to a distal end. Further, the shaft 31 has a proximal end portion 33 and a tapered portion 34. The dilator 30 differs from the dilator 20 in that the dilator 30 does not have a distal end portion.

The proximal end portion 33 and the tapered portion 34 have the same configurations as the proximal end portion 23 and the tapered portion 24. Further, the spirally-arranged protruding portion 32 is provided on an outer peripheral surface 31B of the shaft 31 so as to be protruded outwardly (outermost portion of the dilator 30, the outermost surface). The spirally-arranged protruding portion 32 is provided at a distal end side of the proximal end portion 33 and at the tapered portion 34, and has gaps between adjacent portions along the axis direction of the shaft 31. That is, the adjacent portions of the spirally-arranged protruding portion 32 are spaced from each other. The spirally-arranged protruding portion 32 is integrally formed with the shaft 31 by casting or the like.

Pitches (along the axis A) of adjacent portions of the spirally-arranged protruding portion 32 provided at the tapered portion 34 are configured to be smaller than those of adjacent portions of the spirally-arranged protruding portion 32 provided at the distal end side of the proximal end portion 33. That is, the configuration is such that L31>L32 for the adjacent portions of the spirally-arranged protruding portion 32 wherein L31 represents a pitch at the distal end side of the proximal end portion 33, and L32 represents a pitch at the tapered portion 34. It is noted that the pitches at the distal end side of the proximal end portion 33 may be same or different. The pitches at the tapered portion 34 may be same or different.

In the dilator 30, the spirally-arranged protruding portion 32 protruding outwardly is provided on the outer peripheral surface 31B of the shaft 31, and has gaps between adjacent portions of the spirally-arranged protruding portion 32. This configuration enables the dilator 30 to be moved forward not only by a conventional pushing operation, but also by a rotational operation of the spirally-arranged protruding portion 32.

Further, the pitches of adjacent portions of the spirally-arranged protruding portion 32 provided at the tapered portion 34 are configured to be smaller than those of adjacent portions of the spirally-arranged protruding portion 32 provided at the distal end side of the proximal end portion 33. By virtue of this configuration, the frictional resistance with a target matter (for example, the digestive tract such as stomach, and liver) is larger at the tapered portion 34 of the shaft 31 than at the distal end side of the proximal end portion 34 when the dilator 30 is rotated. This enables a driving force to be larger at the tapered portion 34 than at the proximal end portion 33 of the dilator 30, leading to easy expansion of a hole.

Figure 5:
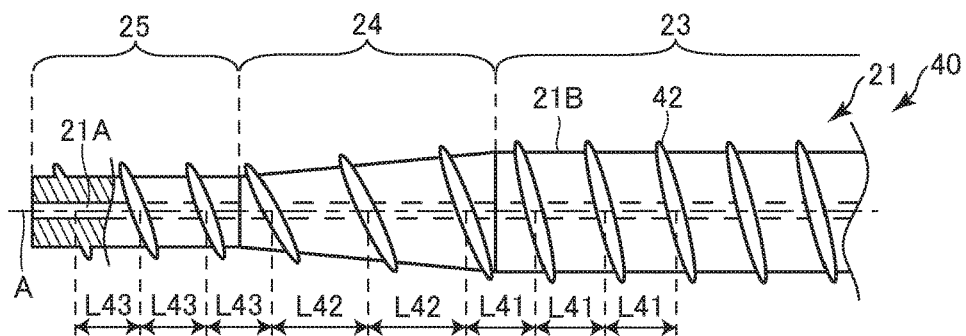
FIG. 5 shows a partial cross-sectional view of a distal-end side portion of a dilator according to the disclosed embodiments.

FIG. 5 shows a partial cross-sectional view of a distal-end side portion of a dilator 40 according to the disclosed embodiments.

In FIG. 5, the left side in the figure corresponds to the front end side (the distal side) which is to be inserted into the body, and the right side corresponds to the base end side (the hand side, the proximal side) which is to be operated by an operator such as a surgeon. It is noted that the same reference number is given to the same member as the third embodiment, and description thereof is omitted.

In FIG. 5, the dilator 40 includes the shaft 21, a spirally-arranged protruding portion 42, and the connector 9 connected to a proximal end of the shaft 21 (see FIG. 3).

The spirally-arranged protruding portion 42 is provided on the outer peripheral surface 21B of the shaft 21 so as to be protruded outwardly (outermost portion of the dilator 40, the outermost surface). The spirally-arranged protruding portion 42 is provided at the distal end side of the proximal end portion 23, at the tapered portion 24, and at the distal end portion 25, and has gaps between adjacent portions of spirally-arranged protruding portion 42 along the axis direction of the shaft 21. That is, the adjacent portions of the spirally-arranged protruding portion 42 are spaced from each other. The spirally-arranged protruding portion 42 is integrally formed with the shaft 21 by casting or the like.

Pitches (along the axis A) of adjacent portions of the spirally-arranged protruding portion 42 provided at the tapered portion 24 are configured to be larger than those of adjacent portions of the spirally-arranged protruding portion 42 provided at the distal end side of the proximal end portion 23 and at the distal end portion 25. That is, the configuration is such that L41, L43<L42 for the adjacent portions of the spirally-arranged protruding portion 42 wherein L41 represents a pitch at the distal end side of the proximal end portion 23, L42 represents a pitch at the tapered portion 24, and L43 represents a pitch at the distal end portion 25. It is noted that the pitches at the distal end side of the proximal end portion 23 and at the distal end portion 25 may be same or different. The pitches at the tapered portion 24 may be same or different.

This configuration also enables the dilator 40 to be moved forward not only by a conventional pushing operation, but also by a rotational operation of the spirally-arranged protruding portion 42.

The pitches of adjacent portions of the spirally-arranged protruding portion 42 provided on the tapered portion 24 are configured to be larger than those of adjacent portions of the spirally-arranged protruding portion 42 provided at the distal end side of the proximal end portion 23 and at the distal end portion 25. By virtue of this configuration, the frictional resistance with a target matter (for example, the digestive tract such as stomach, and liver) is smaller at the tapered portion 24 of the shaft 21 than at the distal end side of the proximal end portion 23 and at the distal end portion 25 when the dilator 40 is rotated. As a result, damages to the target matter due to biting of the target matter may be prevented when a hole is expanded.

Figure 6:
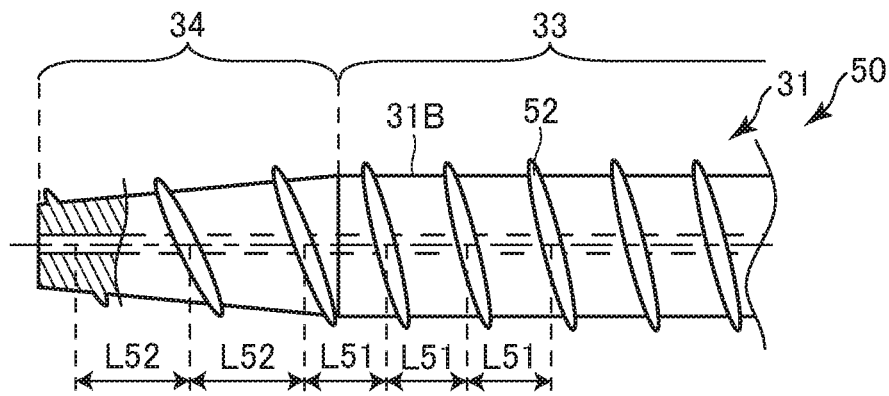
FIG. 6 shows a partial cross-sectional view of a distal-end side portion of a dilator according to the disclosed embodiments.

FIG. 6 shows a partial cross-sectional view of a distal-end side portion of a dilator 50 according to the disclosed embodiments.

In FIG. 6, the left side in the figure corresponds to the front end side (the distal side) which is to be inserted into the body, and the right side corresponds to the base end side (the hand side, the proximal side) which is to be operated by an operator such as a surgeon. It is noted that the same reference number is given to the same member as the fourth embodiment, and description thereof is omitted.

In FIG. 6, the dilator 50 includes the shaft 31, a spirally-arranged protruding portion 52, and the connector 9 connected to the proximal end of the shaft 31 (see FIG. 3).

Further, the spirally-arranged protruding portion 52 is provided on the outer peripheral surface 31B of the shaft 31 so as to be protruded outwardly (outermost portion of the dilator 50, the outermost surface). The spirally-arranged protruding portion 52 is provided at the distal end side of the proximal end portion 33 and at the tapered portion 34, and has gaps between adjacent portions along the axis direction of the shaft 31. That is, the adjacent portions of the spirally-arranged protruding portion 52 are spaced from each other. The spirally-arranged protruding portion 52 is integrally formed with the shaft 31 by casting or the like.

Pitches (along the axis A) of adjacent portions of the spirally-arranged protruding portion 52 provided at the tapered portion 34 are configured to be larger than those of adjacent portions of the spirally-arranged protruding portion 52 provided at the distal end side of the proximal end portion 33. That is, the configuration is such that L51<L52 for the adjacent portions of the spirally-arranged protruding portion 52 wherein L51 represents a pitch at the distal end side of the proximal end portion 33, and L52 represents a pitch at the tapered portion 34. It is noted that the pitches at the distal end side of the proximal end portion 33 may be same or different. The pitches at the tapered portion 34 may be same or different.

This configuration also enables the dilator 50 to be moved forward not only by a conventional pushing operation, but also by a rotational operation of the spirally-arranged protruding portion 52.

Further, the pitches of adjacent portions of the spirally-arranged protruding portion 52 provided at the tapered portion 34 are configured to be larger than those of adjacent portions of the spirally-arranged protruding portion 52 provided at the distal end side of the proximal end portion 33. By virtue of this configuration, the frictional resistance with a target matter (for example, the digestive tract such as stomach, and liver) is smaller at the tapered portion 34 of the shaft 31 than at the distal end side of the proximal end portion 33 when the dilator 50 is rotated. As a result, damages to the target matter due to pinching of the target matter may be prevented when a hole is expanded.

Hereinbefore, the embodiments of the present invention are described, but the present invention shall not be limited to these embodiments. Rather, various modifications may be made.

For example, the first coil 3 is described as a hollow coil body including 10 wires in the aforementioned embodiments, but the number of wires shall not be limited to 10. The number may be one or more. Further, the second coil 5 is described as a hollow coil body including a single wire in the aforementioned embodiments, but the number of wires shall not be limited to 1. The number may be one or more.

Further, the distal tip 6 is described as being formed by casting a solder material into the distal end of the multilayer body 17. However, the outer periphery of the second coil 5 and/or the first coil 3 in the vicinity of the distal end portion of the multilayer body 17 may be ground to form the distal tip 6 having a flat surface.

Furthermore, the distal tip 6 is described above as being fixed to the distal end of the multilayer body 17, but the distal tip may be fixed to the distal end of the shaft 21, or may be fixed to the distal end of the shaft 31.

Figure 7:
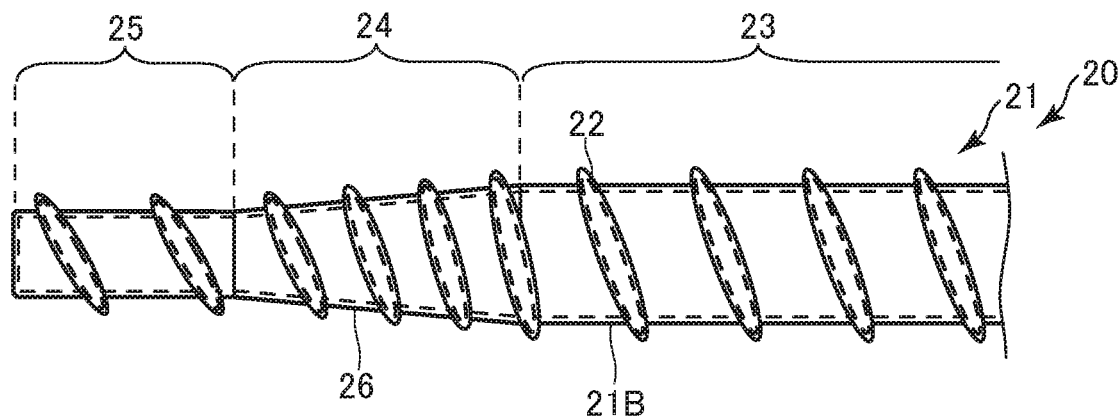
FIG. 7 shows a dilator according to the disclosed embodiments.

Further, the outer peripheries of the multilayer bodies 7 and 17, the shafts 21 and 31, and the spirally-arranged protruding portions 22, 32, 42, and 52 may be coated with a resin(s). For example, as shown in FIG. 7, the outer peripheries of the shaft 21 and the spirally-arranged protruding portion 22 of the dilator 20 may be coated with a resin 26. The resin 26 can improve slidability to prevent pinching of a living body tissue. When the outer periphery of the shaft 21 is coated with the resin 26, a portion where the proximal end portion 23, the tapered portion 24, and the distal end portion 25 are coated with the resin 26 corresponds to the shaft 21, and a portion protruding outwardly from the outer peripheral surface 21B of the shaft 21 corresponds to the spirally-arranged protruding portion 22. Examples of the resin 26 include, for example, biocompatible resin materials such as polyamide resin and fluororesin, hydrophilic coating materials, or the like. The resin 26 has a thickness of, for example, 0.1 to 300 μm. Further, the shafts 21 and 31 and the spiral protruding portions 22, 32, 42, and 52 are formed integrally, but may be formed as separate bodies.

Figure 8:
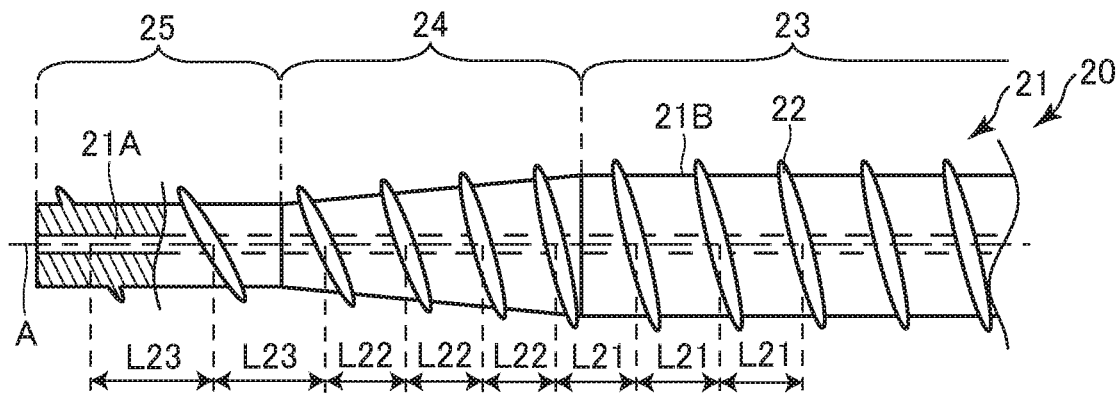
FIG. 8 shows a dilator according to the disclosed embodiments.

Further, with regard to the spirally-arranged protruding portion 22 of the dilator 20 as shown in FIG. 3, the pitches of adjacent portions of the spirally-arranged protruding portion 22 provided at the tapered portion 24 are configured to be smaller than those of adjacent portions of the spirally-arranged protruding portion 22 provided at the distal end side of the proximal end portion 23 and at the distal end portion 25. However, as shown in FIG. 8, the pitches (L21, L22) of adjacent portions of the spirally-arranged protruding portion 22 provided on the tapered portion 24 and at the distal end side of the proximal end portion 23 may be configured to be smaller than the pitch (L23) of adjacent portions of the spirally-arranged protruding portion 22 provided on the distal end portion 25. That is, pitches may be configured so as to be L23>L21, L22. It is noted that the pitches at the distal end portion 25 may be same or different. The pitches at the tapered portion 24 and distal end side of the proximal end portion 23 may be same or different. This configuration enables a driving force to be larger at the tapered portion 24 than at the distal end portion 25 of the dilator 20, leading to easy expansion of a hole.

Figure 9:
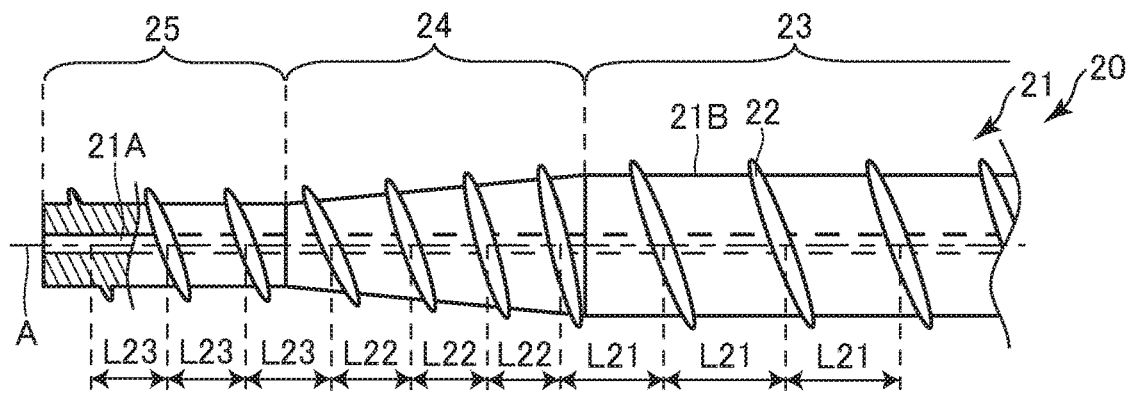
FIG. 9 shows a dilator according to the disclosed embodiments.

Alternatively, as shown in FIG. 9, the pitches (L22, L23) of adjacent portions of the spirally-arranged protruding portion 22 provided on the tapered portion 24 and the distal end portion 25 may be configured to be smaller than the pitch (L21) of adjacent portions of the spirally-arranged protruding portion 22 provided at the proximal end portion 23. That is, pitches may be configured so as to be L21>L23, L22. It is noted that the pitches at the distal end side of the proximal end portion 23 may be same or different. The pitches at the tapered portion 24 and the distal end portion 25 may be same or different. This configuration enables a driving force to be larger at the tapered portion 24 than at the proximal end portion 23 of the dilator 20, leading to easy expansion of a hole.

Figure 10:
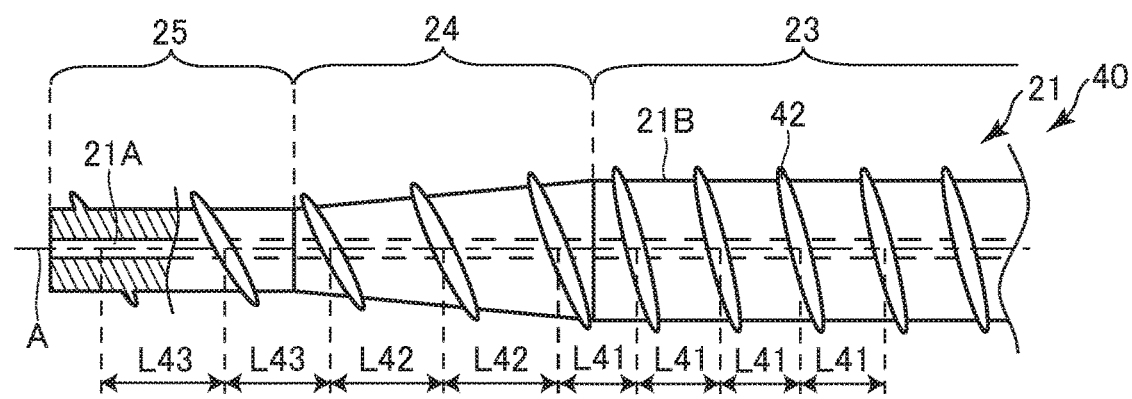
FIG. 10 shows a dilator according to the disclosed embodiments.

Further, with regard to the spirally-arranged protruding portion 42 in the dilator 40 as shown in FIG. 5, the pitches of adjacent portions of the spirally-arranged protruding portion 42 provided on the tapered portion 24 are configured to be larger than those of adjacent portions of the spirally-arranged protruding portion 42 provided at the distal end side of the proximal end portion 23 and at the distal end portion 25. However, as shown in FIG. 10, the pitches (L42, L43) of adjacent portions of the spirally-arranged protruding portion 22 provided on the tapered portion 24 and the distal end portion 25 may be configured to be larger than the pitch (L41) of adjacent portions of the spirally-arranged protruding portion 22 provided at the distal end side of the proximal end portion 23. That is, pitches may be configured so as to be L43, L42>L41. It is noted that the pitches at the distal end side of the proximal end portion 23 may be same or different. The pitches at the tapered portion 24 and the distal end portion 25 may be same or different. By virtue of this configuration, the frictional resistance with a target matter (for example, the digestive tract such as stomach, and liver) is smaller at the tapered portion 24 of the shaft 21 than at the distal end side of the proximal end portion 23 when the dilator 50 is rotated. As a result, damages to the target matter due to pinching of the target matter may be prevented when a hole is expanded.

Figure 11:
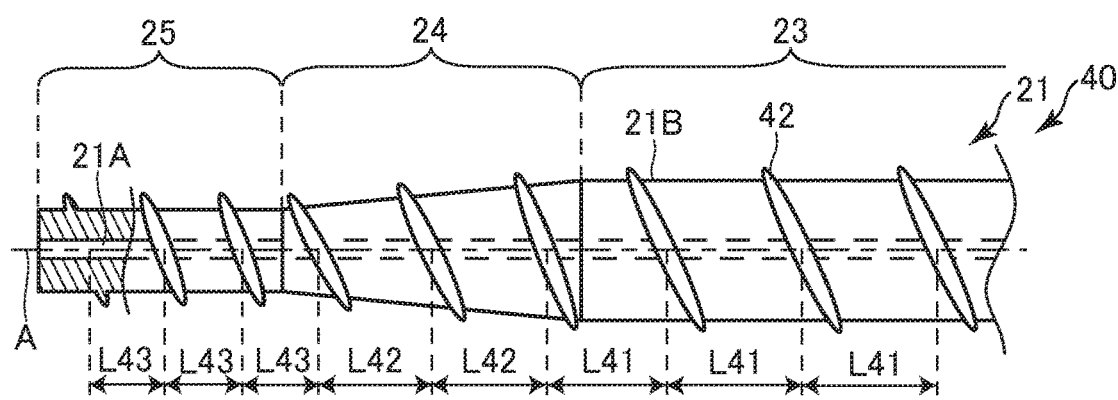
FIG. 11 shows a dilator according to the disclosed embodiments.

Alternatively, as shown in FIG. 11, the pitches (L41, L42) of adjacent portions of the spirally-arranged protruding portion 22 provided on the tapered portion 24 and the distal end side of the proximal end portion 23 may be larger than the pitch (L43) of adjacent portions of the spirally-arranged protruding portion 22 provided at the distal end portion 25. That is, pitches may be configured so as to be L41, L42>L43. It is noted that the pitches at the distal portion 25 may be same or different. The pitches at the tapered portion 24 and the distal end side of the proximal end portion 23 may be same or different. By virtue of this configuration, the frictional resistance with a target matter (for example, the digestive tract such as stomach, and liver) is smaller at the tapered portion 24 of the shaft 21 than at the distal end side of the proximal end portion 25 when the dilator 50 is rotated. As a result, damages to the target matter due to pinching of the target matter may be prevented when a hole is expanded.

The shaft may have various types of coating on the side of the surface thereof (including a portion between the shaft and the spirally-arranged protruding portion). Examples of the coating include, for example, a protective film on the surface of the shaft (representative example: a plating film), an underlying film for improving adhesiveness between the shaft and the spirally-arranged protruding portion, and the like.

Preferably, the dilators shown in FIGS. 1 to 11 are not configured to serve as a blade. The dilators according to the present embodiments are intended for expanding a hole pre-formed in a target matter (for example, the wall of the digestive tract such as the patient's stomach). Therefore, if the spirally-arranged protruding portion serves as a blade, living body tissues at the inner surface of the hole may be damaged.

For this reason, the spirally-arranged protruding portion preferably does not have a sharp edge at an end portion on a radially outer side of the shaft in a cross-section (for example, in a cross-section perpendicular to the spiral direction of the spirally-arranged protruding portion as shown in FIG. 3). That is, the above end portion preferably has an area having a shape including an obtuse edge or a curve (for example, a curve constituting a part of a circle or an ellipse). Thus, the spirally-arranged protruding portion is configured so as not to cut living tissue when dilating a hole pre-formed in a target object.

What is claimed is:

1. A dilator comprising:
   a hollow shaft comprising a first coil having a wire wound around into a hollow shape including:
      a tapered portion having an outer diameter that is smaller at a distal end of the tapered portion than at a proximal end of the tapered portion;
      a proximal end portion provided at a proximal end side of the tapered portion and extending in a proximal direction; and
      optionally, a distal end portion provided at a distal end side of the tapered portion and extending in a distal direction;
   a spirally-arranged protruding portion provided on an outer peripheral surface of the shaft and forming an exterior surface of the dilator, the spirally-arranged protruding portion protruding radially outward from the shaft and having gaps between adjacent portions of the spirally-arranged protruding portion along a longitudinal axis of the shaft; and
   a grip portion provided on a proximal end of the shaft, wherein:
   in a case where the shaft does not include the distal end portion, pitches of adjacent portions of the spirally-arranged protruding portion provided on the tapered portion are different than pitches of adjacent portions of the spirally-arranged protruding portion provided on a distal end side of the proximal end portion, and
   in a case where the shaft includes the distal end portion, the pitches of adjacent portions of the spirally-arranged protruding portion provided on the tapered portion are different than pitches of adjacent portions of the spirally-arranged protruding portion provided on the distal end portion and/or the pitches of adjacent portions of the spirally- arranged protruding portion provided on the distal end side of the proximal end portion.

2. The dilator according to claim 1, wherein:
in the case where the shaft does not include the distal end portion, the pitches of adjacent portions of the spirally-arranged protruding portion provided on the tapered portion are smaller than the pitches of adjacent portions of the spirally-arranged protruding portion provided on the distal end side of the proximal end portion, and
in the case where the shaft includes the distal end portion, the pitches of adjacent portions of the spirally-arranged protruding portion provided on the tapered portion are smaller than the pitches of adjacent portions of the spirally-arranged protruding portion provided on the distal end portion and/or the pitches of adjacent portions of the spirally- arranged protruding portion provided on the distal end side of the proximal end portion.

3. The dilator according to claim 2, wherein:
in the case where the shaft includes the distal end portion, the pitches of adjacent portions of the spirally-arranged protruding portion provided on the tapered portion are smaller than the pitches of adjacent portions of the spirally-arranged protruding portion provided at the distal end portion and at the distal end side of the proximal end portion.

4. The dilator according to claim 1, wherein:
in the case where the shaft does not include the distal end portion, the pitches of adjacent portions of the spirally-arranged protruding portion provided on the tapered portion are larger than the pitches of adjacent portions of the spirally-arranged protruding portion provided on the distal end side of the proximal end portion, and
in the case where the shaft includes the distal end portion, the pitches of adjacent portions of the spirally-arranged protruding portion provided on the tapered portion are larger than the pitches of adjacent portions of the spirally-arranged protruding portion provided on the distal end portion and/or the pitches of adjacent portions of the spirally- arranged protruding portion provided on the distal end side of the proximal end portion.

5. The dilator according to claim 4, wherein:
in the case where the shaft includes the distal end portion, the pitches of adjacent portions of the spirally-arranged protruding portion provided on the tapered portion are larger than the pitches of adjacent portions of the spirally-arranged protruding portion provided at the distal end portion and at the distal end side of the proximal end portion.

6. The dilator according to claim 1, wherein the spirally-arranged protruding portion includes a second coil having a wire wound around on the outer peripheral surface of the shaft.

7. The dilator according to claim 6,
wherein the wire of the first coil is wound around in a direction opposite to the wire of the second coil.

* * * * *